Figure 1:
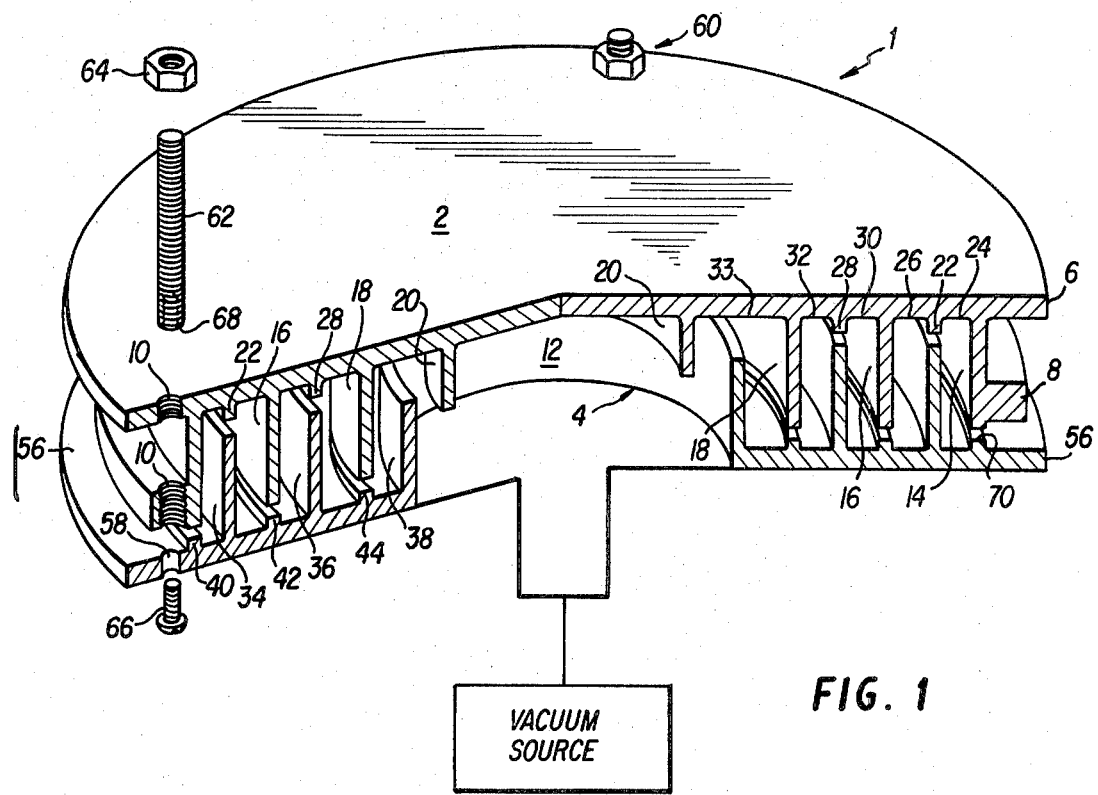

United States Patent [19]

Bell

[11] 4,400,982
[45] Aug. 30, 1983

[54] HIGH VOLUME PARTICLE COLLECTOR AND FRACTIONATOR

[75] Inventor: John P. Bell, Raleigh, N.C.

[73] Assignee: The United States of America as represented by the Environmental Protection Agency, Washington, D.C.

[21] Appl. No.: 291,724

[22] Filed: Aug. 10, 1981

[51] Int. Cl.³ .......................... G01N 1/24; G01N 15/02
[52] U.S. Cl. ..................................... 73/863.22; 55/270
[58] Field of Search ................... 73/863.22, 28, 863.21, 73/863.41, 863.51; 55/270, 274

[56] References Cited

U.S. PATENT DOCUMENTS

| | | | |
|---|---|---|---|
| 2,538,116 | 1/1951 | May | 73/28 |
| 3,144,315 | 8/1964 | Hunn | 55/274 |
| 3,693,457 | 9/1972 | Pilat | 73/28 X |
| 3,795,135 | 3/1974 | Anderset | 73/28 |
| 3,823,602 | 7/1974 | Anderson | 73/28 |
| 3,938,366 | 2/1976 | Wertlake et al. | 73/28 |
| 3,949,594 | 4/1976 | Treaftis et al. | 73/28 |
| 3,953,182 | 4/1976 | Roth | 73/28 X |
| 3,985,624 | 10/1976 | Prevost et al. | 73/863.21 X |
| 4,133,202 | 1/1979 | Marple | 73/28 |
| 4,189,937 | 2/1980 | Nelson | 73/28 |
| 4,279,156 | 7/1981 | Bell | 73/863.22 |

Primary Examiner—E. R. Kazenske
Assistant Examiner—Tom Noland

[57] ABSTRACT

A particle collector and fractionator having a 360° omnidirectional gas inlet slit is disclosed herein. The collector and fractionator generally comprises a top and bottom fractionating member, each of which has a set of concentric, annular ring projections which are complementary to the other set. The ring projections form channels in the top and bottom members. The collector has at least one standoff for fastening together and spacing the top and bottom fractionating members. The concentric, annular ring projections form rectangular-shaped slits, when viewed in a cross-section. The slits, formed as they are by the ring-like projections, define a gas flow path from the omnidirectional gas inlet slit to a centrally disposed gas outlet port. Particles are collected and fractionated in the channel portions of the concentric, annular ring-like projections whenever particle laden gas flows into the gas flow path and out through the centrally disposed gas port. The minimum aerodynamic size of the particles collected and fractionated may be selected by adjusting the stand-offs so as to vary the cross-sectional area of the gas flow path, which in turn increases or decreases the velocity of a stream of particle laden gas flowing through the path. The cross-sectional areas may all be adjusted simultaneously by the use of the stand-offs.

10 Claims, 2 Drawing Figures

HIGH VOLUME PARTICLE COLLECTOR AND FRACTIONATOR

BACKGROUND OF THE INVENTION

Reference is made to applicant's related application Ser. No. 89,011, now U.S. Pat. No. 4,279,156.

This invention relates to particle collectors and fractionators for both collecting and fractionating particles from a stream of gas. While the invention disclosure may be used in any application requiring the separation of particulate matter from a gaseous medium, the invention is specifically designed for separating and fractionating fine particles of pollutants from the atmosphere incident to air sampling tests.

The particle collector and fractionator should be easy to clean and of simple construction, but nonetheless capable of accurately fractionating and effectively collecting a group of gas suspended particles into a large number of discrete categories of aerodynamic diameters. The accuracy of a particle collector and fractionator is particularly important, and when the collector is being used to collect particles of pollutants from the atmosphere, the accuracy of the particle density measurements should not be affected by air currents. Also, a collector should be convenient and simple to operate either by itself, or in combination with particle filters or other forms of conventional particle collecting and sampling equipment. Another desirable feature of any particle collector and fractionator is its ability to be adjustable for collecting and fractionating particles over a wide range of minimum aerodynamic size. Finally, such a collector should be capable of handling a high volume mass flow rate so as to allow large samples to be taken for biological and chemical analysis.

SUMMARY OF THE INVENTION

This invention concerns a particle collector and fractionator which generally comprises a top and bottom fractionating member, each member having a set of concentric, annular channels which are complementary in shape to the other member. The top and bottom members are assembled together by a series of standoffs which are comprised of a calibrated threaded member received in flange portions of the top member. A lock nut engages a protruding section of the calibrated screw which protrudes through the top surface of the top member. A lock screw, located in a flange portion of the bottom member, passes through the bottom member and threadedly engages with an end portion of the calibrated member which abuts the bottom member flange. When the top and bottom members are assembled in this spaced relationship, a concentric gas flow path is formed between the members. The entrance to the gas flow path is defined around the adjacent edges of the spaced part top and bottom fractionating members in a 360° omnidirectional gas slit. The invention also includes a gas withdrawal means, located radially inwardly along the gas flow path, for withdrawing particle laden gas from the center of the gas flow path. The gas withdrawal means includes a gas port centrally located in the concentric channels of the top and bottom fractionating members which is fluidly connected to a source of negative pressure.

When a stream of particle laden gas enters the omnidirectional gas slit and flows through the gas flow path defined between the complementary channels of the top and bottom fractionating members, particles in the gas stream impact on upright members forming the channels and are collected in the channel portions as they attempt to negotiate the rectangular-shaped slits which lead from one channel to the next.

The minimum aerodynamic size of the particles collected in the channels may be selected by adjusting the calibrated stand-offs so as to vary the radial velocity of the gas stream flowing through the flow path by increasing or decreasing the cross-sectional area of the rectangular-shaped flow path between the concentric, annular channels. Assuming that the invention is constructed so that the rectangular-shaped openings, in the channel members, are of a constant width from the outermost to the centermost channel, the radial velocity of the gas stream remains substantially constant at each point as the stream converges towards the centrally disposed gas port outlet. Consequently, particles of progressively smaller aerodynamic sizes are collected in each successive channel portion.

The particle collector and fractionator of the invention is also designed to operate at a high volume flow rate which will allow particles to be separated which are larger than 2.5 microns from those which are smaller in cases where the flow rate is greater than 20 liters per minute and less than 2,000 liters per minute. Also, because the high volume fractionator has a different geometry, due to the rectangularly-shaped slits, a more turbulent flow is created within the fractionator and that in combination with the difference in geometry allows the high volume fractionator to be made much more compact. For example, a 1,500 liter per minute high volume fractionator is about the same size as a 15 liter per minute fractionator instead of being about 100 times larger.

The particle collector and fractionator of the invention is thus simple in construction, easy to use, and may be easily cleaned by simply detaching the stand-off members and separating and cleaning the top and bottom fractionating members. As the invention contemplates the use of multiple sets of complementary concentric channels, it is easily capable of fractionating particles in a stream of gas into multiple discrete categories. Also, the adjustability of the stand-off members allow all of the fractionating stages to be adjusted simultaneously. Finally, the use of a 360° omnidirectional gas slit provides a particle collector and fractionator whose particle density measurements are essentially unaffected by the direction of air currents.

BRIEF DESCRIPTION OF THE DRAWINGS

FIG. 1 is a perspective, partial cross-sectional view of the preferred embodiment of the invention; and FIG. 2 is a cross-sectional view taken between the center line and the outer circumferential edge of the invention.

DETAILED DESCRIPTION OF THE DRAWINGS

With reference to FIG. 1, the particle collecting and fractionating device is shown generally at 1. The top fractionating member 2 and the bottom fractionating member 4 are shown with each having a plurality of interdigitated elements as will be further explained below. The top member 2 is circumferential in shape with its radially outer edge portion defined by two flange portions 6 and 8. At equally spaced locations, around the flange edge portions 6 and 8, are a series of threaded openings 10, the purpose of which will be further explained below. On the bottom side 12 of the top member 2, and formed integrally therewith, is a series of concentric, annular, downwardly-extending rings 14, 16, 18 and 20. The ring 14 defines the outer circumferential wall of the top member 2. The ring 20 defines the inner circumferential wall of the member 2, with ring projections 16 and 18 interspersed therebetween. Located between ring projections 14 and 16, is a shorter, downwardly-extending ring projection 22 which defines channels 24 and 26 formed by the downwardly-extending ring projections 14, 16 and 22. Similarly, a second short, downwardly-extending ring projection is shown at 28 which defines channels 30 and 32 in conjunction with the longer ring projections 16 and 18. A fifth channel 33 is formed between ring projections 18 and 20.

The bottom member 4 has a similar series of longer ring projections 34, 36 and 38. However, these projections are complementary to those described above in that they extend upwardly from the bottom member 4 into an interdigitated arrangement with the longer projections 14, 16 and 18 of the top member 2. The longer projections, of the bottom member 4, extend upwardly and directly in line with the short projections 22, 28 of the top member 2. Since these in-line projections are not allowed to abut when the particle collector and fractionator is assembled in working order, a rectangular-shaped slit, when viewed in cross section-section, is formed therebetween. The slits will be explained in further detail below. Also formed on the bottom member 4 are a series of shorter projections 40, 42, and 44 which have the same thickness and length as the shorter projections 22, 28 formed on the top member 2. The shorter projections 40, 42, and 44 on the bottom member 4 extend upwardly but do not engage with the longer projections 14, 16 and 18 of the top member 2. By forming the projections in this manner, rectangular-shaped slits are provided in a manner similar to that described above.

In between the long and short projections, of the just described bottom member 4, is formed a series of channels 46, 48, 50, 52 and 54. The bottom member 4 is also provided, at its outermost, radial extent, with a flange 56 which is provided with a series of apertures 58 that will be aligned with the threaded openings 10 in the flange members 6 and 8 of the top member 2 when the members 2 and 4 are in an assembled relationship.

In order to assemble the members 2 and 4, a series of stand-offs 60 are provided at selected points along the flange areas 6, 8 and 10 of the members 2 and 4. The stand-offs 60 consist of a threaded member 62, a lock nut 64, and a second threaded member 66. The threaded member 62 is adapted to threadedly engage with the threaded openings 10 in the flange portions 6 and 8 of the top member 2. The threaded member 62 is inserted through the openings 10 until the bottom portion 68 abuts the flange 56 on the bottom member 4. At this point, it is aligned with openings 58 in the flange 56 and the second threaded member 66 is inserted through the aperture 58 and threadedly engaged interiorly of the threaded member 62. Lock nuts 64 are then placed in position on the member 62 and tightened until they are in flush engagement with the member 2.

Figure 2:
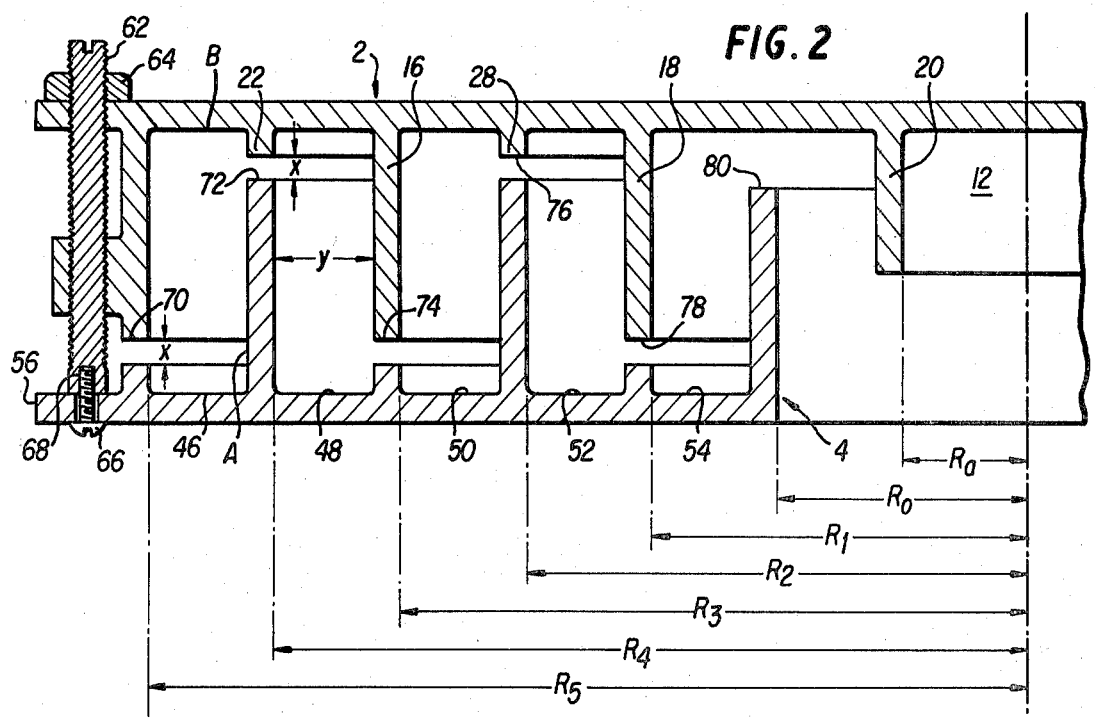

In operation, and in conjunction with FIG. 2, the members 2 and 4 are assembled together in spaced relationship so as to define a constant width rectangular-shaped, in cross-section, opening 70 which functions as a 360° omnidirectional gas inlet slit.

In operation, particle laden gas enters the particle collector and fractionator 1 from any point along the 360° omnidirectional gas inlet slit 70. The gas is then drawn through the concentric, annular channels defined by the projections on the top and bottom members 2 and 4. The gas travels radially, along the radial distance $R_5$, through the labyrinth of rectangular-shaped cross-sections 70, 72, 74, 76, 78 and 80 towards a gas outlet port 12. As the particle laden gas travels through the gas flow path, the particles are forced to make sharp turns between each of the channel portions and ring projections of the top 2 and bottom 4 of the interdigitated fractionating members. Additionally, the particles are required to slow down at the channel portions due to the fact that the cross-section of the gas flow path widens at each of these channel portions. The difference in flow path width is clearly illustrated in FIG. 2 where X represents the width of the rectangular-shaped slits and Y represents the distance between the channel portions formed by the ring projections of the top and bottom members 2, 4.

Assuming that the gas withdrawal port 12 is fluidly connected to a source of constant, negative pressure, adjusting the relative height of the top fractionating member 2 over the bottom fractionating member 4 will in turn vary the width X of the gas flow path 70, 72, 74, 76, 78 and 80. By varying the width, the velocity of a stream of particle laden gas will increase or decrease during its traversal from the inlet port 70 of the 360° gas slit to the outlet port 12. In order to provide for precise adjustment of the top member 2 relative to the bottom member 4 and, consequently, precisely adjusting the rectangular-shaped slits in the X direction, the threaded member 62 may be considered calibrated by knowing the exact pitch and threads per inch of the member 62. Therefore, the slit distance X may be adjusted by adjusting the stand-off member 60. Additionally, the slit width X may be adjusted by the use of a feeler gauge inserted in the slit 70. Such variations in gas stream velocity will in turn determine the minimum aerodynamic size of the particles to be collected and fractionated in channel portions, 46, 48, 50, 52 and 54. As used in this specification, the term "aerodynamic size" refers to the diameter of a sphere of unit density which has the same terminal velocity as the particle in question in an identical carrying gas.

Further operation will be illustrated by the following example. The design is intended to have a $D_{50}$ particle cutoff size, i.e., the particle size at which 50% of the particles are collected and 50% penetrate. Also, it is assumed that the desired flow is 50 SCFM and that particles smaller than 2.5 microns are to be collected on a downstream filter located in the outlet 12. Under these conditions, air particles will enter the slit 70 at 850 centimeters per second and those smaller than 3.8 microns continue to the slit 72. A large percentage, approximately 90%, of those particles larger than 3.8 microns impact on the ring projection 34 near point A. Of the remaining 10% of these large particles, a large percentage of those larger than 4.7 microns will impact at point B. Thus, in the first channel 46, particles larger than 4.7 microns were fractionated twice and approximately 99% were removed. Those particles larger than 3.8 microns were fractionated once with approximately 90% removed.

The second channel performs the same function as the first channel except smaller particles are fractionated. Thus, particles which follow the path to the second stage, about 1% of those larger than 4.7 microns, are again fractionated but this time at a smaller $D_{50}$ at slit 72.

This process of selectively removing the larger particles continues until the last fractionation channel where the final fractionation at 2.5 microns occurs. By this time virtually all of the large particles have been removed and almost all particles smaller than 2.5 microns remain in the air stream. Those particles less than 2.5 microns then pass with the air stream, through the outlet 12, to a filter where they are collected.

In view of this example, it should be noted that the adjustable particle collector and fractionator serves to simultaneously adjust the minimum aerodynamic particle size at each of the channels 46, 48, 50, 52 and 54. Further, it should also be apparent that the particle collector and fractionator of the invention will work equally well if the stream of particle laden gas enters port 12 and exits the 360° omnidirectional gas slit 70. Also, it should be apparent that the invention could work equally well in conjunction with a source of negative or positive pressure at either port 12 or slit 70.

In considering the invention, it will be understood that the invention is not limited to the particular embodiment described in detail above or to any particular number of stages or materials, but only by the following set of claimed definitions.

I claim:

1. A particle collector and fractionator, comprising:

(a) a bottom member having a plurality of concentric, annular channels;

(b) a top member having a plurality of concentric, annular channels which are complementary to said concentric, annular channels of said bottom member;

(c) adjustable fastening means threadedly engaged with said top member for securing said top and bottom members together in an interdigitated relationship so as to form a plurality of rectangular-shaped openings which define a gas flow path therebetween for receiving a particle laden gas;

(d) an inlet located radially outwardly of said rectangular-shaped gas flow path for receiving said particle laden gas;

(e) an outlet located radially inwardly of said rectangular-shaped gas flow path for withdrawing said particle laden gas;

whereby particles in a stream of said particle laden gas are collected in said channels defined by said interdigitated top and bottom members.

2. The particle collector and fractionator of claim 1 wherein said outlet is disposed in the center of said concentric, annular channels of said bottom member.

3. The particle collector and fractionator of claim 1 wherein said outlet is connected to a source of constant, negative fluid pressure.

4. The particle collector and fractionator of claim 1 wherein the rectangular-shaped gas flow path between each of the complementary channels is substantially equal at any point along the radius of said concentric annular channels;

whereby the minimum aerodynamic size of the particles fractionated in each of the channel portions becomes successively smaller as the gas flow path approaches the outlet.

5. The particle collector and fractionator of claim 1 wherein said adjustable fastening member is a calibrated member which threadedly engages two flange portions defining the outer circumferential edge of said top member.

6. The particle collector and fractionator of claim 5 wherein the minimum aerodynamic size of the particle fractionated in each channel may be selected by adjusting said calibrated member.

7. The particle collector and fractionator of claim 6 wherein said calibrated member simultaneously adjusts the width of said plurality of rectangular-shaped openings;

whereby the range of minimum aerodynamic sizes of particles fractionated in each of the channels may be selected by adjusting said calibrated member.

8. The particle collector and fractionator of claim 1 wherein said top and bottom members each include five channels.

9. The particle collector and fractionator of claim 1 wherein at least five rectangular-shaped openings are provided for defining said gas flow path.

10. The particle collector and fractionator of claim 5 wherein an end portion of said calibrated member abuts a flange portion defining the outer circumferential edge of said bottom member, said calibrated member secured to said bottom member by securing means passing through said bottom member flange and engaging said calibrated member.

* * * * *